(12) United States Patent
Brown et al.

(10) Patent No.: US 11,643,796 B2
(45) Date of Patent: May 9, 2023

(54) TEMPORARY RESTROOM AND WELLNESS POD

(71) Applicant: Lendlease Americas Inc., New York, NY (US)

(72) Inventors: Theresa L. Brown, Charlotte, NC (US); Glenn T. Clarke, Monee, IL (US)

(73) Assignee: Lendlease Americas Inc., New York, NY (US)

( * ) Notice: Subject to any disclaimer, the term of this patent is extended or adjusted under 35 U.S.C. 154(b) by 400 days.

(21) Appl. No.: 16/911,985

(22) Filed: Jun. 25, 2020

(65) Prior Publication Data

US 2021/0180300 A1 Jun. 17, 2021

Related U.S. Application Data

(60) Provisional application No. 62/947,728, filed on Dec. 13, 2019.

(51) Int. Cl.
*E03C 1/01* (2006.01)
*E03C 1/182* (2006.01)
(Continued)

(52) U.S. Cl.
CPC ............... *E03C 1/01* (2013.01); *A47K 5/12* (2013.01); *A47K 10/32* (2013.01); *A61L 2/0088* (2013.01);
(Continued)

(58) Field of Classification Search
CPC .. E03C 1/01; E03C 1/182; A47K 5/12; A47K 10/32; A47K 4/00; A61L 2/10;
(Continued)

(56) References Cited

U.S. PATENT DOCUMENTS 2,037,895 A * 4/1936 Ericgugler .......... E04B 1/34869
52/36.2
2,712,863 A * 7/1955 Frankw ............... E04B 1/34869
4/663
(Continued)

FOREIGN PATENT DOCUMENTS

CN 107762188 A 3/2018

OTHER PUBLICATIONS

"Incinerator Restroom," NuConcepts, Feb. 2018.
(Continued)

*Primary Examiner* — Benjamin R Shaw
(74) *Attorney, Agent, or Firm* — Merchant & Gould P.C.

(57) ABSTRACT

A temporary restroom may form a complete enclosure, including a front wall, a back wall, two sidewalls, a floor, a ceiling, and a door. The front wall, the back wall, the two sidewalls, the floor and the ceiling each includes multiple support members, which together form a frame. Inside the enclosure, the temporary restroom includes a, coupled with a waste drainage pipe, a sink in, coupled with a water pipe and a waste water drainage pipe, and multiple connections for connecting the waste drainage pipe and the waste drainage pipe to waste plumbing, connecting the water pipe to water plumbing, and connecting the temporary restroom to a source of electric power. The temporary restroom does not include a waste storage tank or a built-in source of water.

19 Claims, 11 Drawing Sheets

(51) Int. Cl.
  *E03D 9/04* (2006.01)
  *A47K 5/12* (2006.01)
  *A47K 10/32* (2006.01)
  *A61L 2/10* (2006.01)
  *A61L 2/24* (2006.01)
  *A61L 2/00* (2006.01)
  *E04H 1/12* (2006.01)
  *E03D 7/00* (2006.01)

(52) U.S. Cl.
  CPC .............. *A61L 2/10* (2013.01); *A61L 2/24* (2013.01); *E03C 1/182* (2013.01); *E03D 9/04* (2013.01); *E04H 1/1216* (2013.01); *A61L 2202/11* (2013.01); *A61L 2202/14* (2013.01); *A61L 2202/25* (2013.01); *E03D 7/00* (2013.01)

(58) Field of Classification Search
  CPC ... A61L 2202/14; A61L 2202/25; E03D 9/04; E03D 7/00; E04H 1/1216; E04B 1/34869
  USPC .......................................................... 4/664
  See application file for complete search history.

(56) References Cited

U.S. PATENT DOCUMENTS

| | | | | |
|---|---|---|---|---|
| 3,110,907 A * | 11/1963 | King | .................. | E04B 1/34869 4/300 |
| 3,162,863 A * | 12/1964 | Wokas | ................ | E04B 1/34869 4/252.2 |
| 3,601,821 A * | 8/1971 | Corsiglia | .................. | E03D 7/00 4/300 |
| 3,727,753 A * | 4/1973 | Starr | ................... | E04B 1/34869 52/79.5 |
| 4,788,802 A * | 12/1988 | Wokas | ................ | E04B 1/34869 52/34 |
| 6,681,413 B2 | 1/2004 | Weiss | | |
| 9,340,963 B2 | 5/2016 | Ito et al. | | |
| 9,879,437 B2 | 1/2018 | Ito et al. | | |
| 9,909,293 B2 | 3/2018 | Winter et al. | | |
| 10,036,172 B1 | 7/2018 | Baker | | |
| 10,066,409 B2 | 9/2018 | Sansom, III et al. | | |
| 11,248,370 B1 * | 2/2022 | Hillje | ...................... | E03C 1/122 |
| 2004/0010847 A1 * | 1/2004 | Braxton | ................ | E04H 1/1216 4/664 |
| 2007/0130686 A1 * | 6/2007 | Merz | ...................... | B60R 15/00 4/664 |
| 2009/0100769 A1 * | 4/2009 | Barrett | ................ | E04B 1/34869 52/745.13 |
| 2010/0043309 A1 * | 2/2010 | Martin | ...................... | E03C 1/01 52/79.5 |
| 2010/0212082 A1 * | 8/2010 | Tyler | ..................... | E04H 1/1216 4/476 |
| 2013/0232685 A1 * | 9/2013 | Cornille | .................... | A47K 4/00 4/663 |
| 2014/0215702 A1 * | 8/2014 | Ito | ............................. | E03D 7/00 4/321 |
| 2017/0107730 A1 * | 4/2017 | Sansom, III | .......... | E04H 1/1216 |
| 2017/0143169 A1 * | 5/2017 | Braxton | .............. | E04B 1/34336 |
| 2017/0159276 A1 * | 6/2017 | Ito | ............................. | A47K 1/02 |
| 2017/0226722 A1 * | 8/2017 | Marcel | ...................... | E03D 7/00 |
| 2018/0238046 A1 * | 8/2018 | Hillje | ...................... | A47K 4/00 |
| 2021/0059480 A1 * | 3/2021 | Blevins | .................... | A47K 4/00 |
| 2021/0372117 A1 * | 12/2021 | Littow | .................... | H02S 20/32 |

OTHER PUBLICATIONS

"WB Model 240 Volt Incinerator Restroom Specifications," NuConcepts, Feb. 2018.

Int'l Search Report and Written Opinion of the Int'l Searching Authority, Appln No. PCT/US2020/049217, dated Dec. 17, 2020, 15 pages.

* cited by examiner

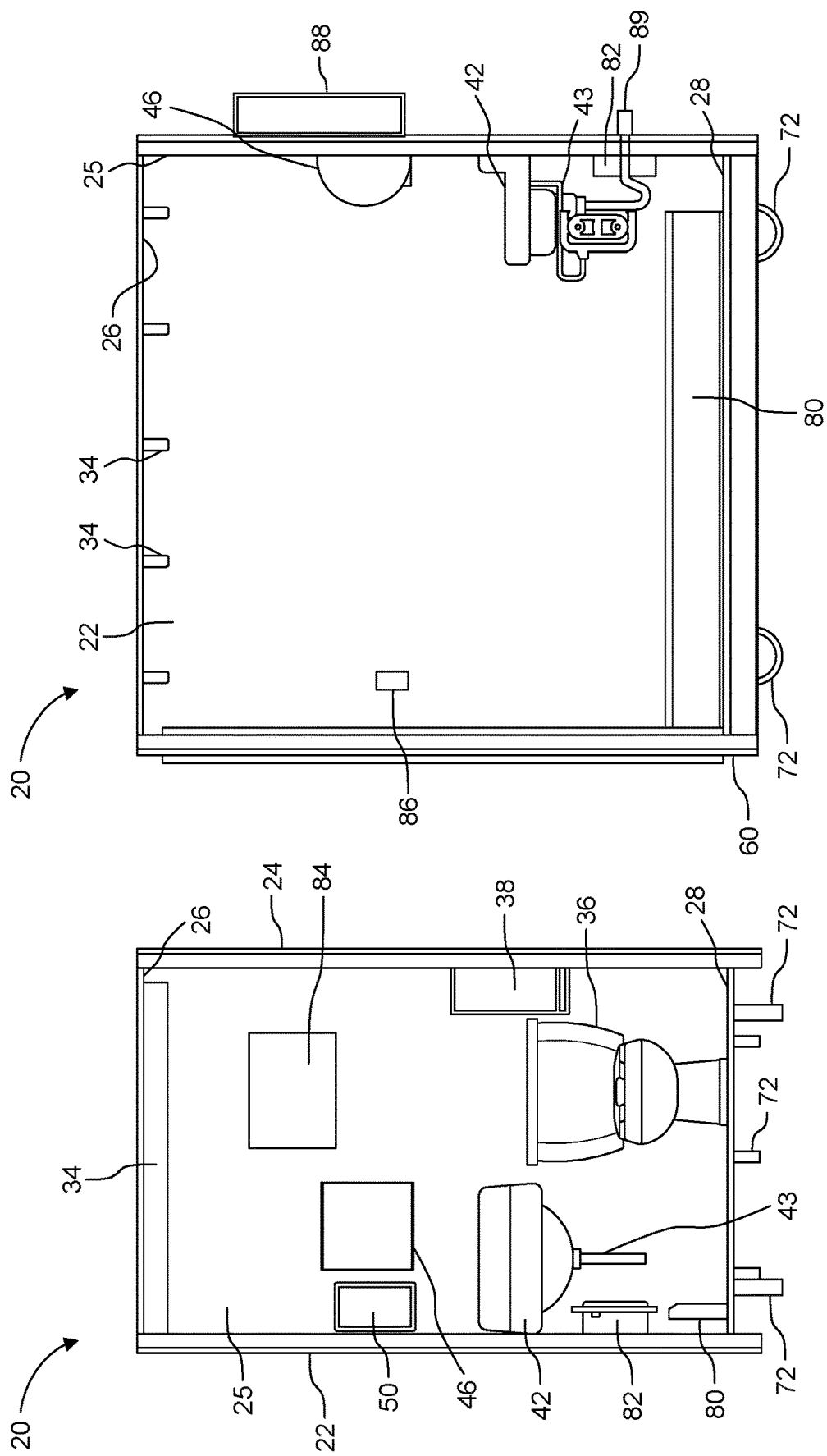

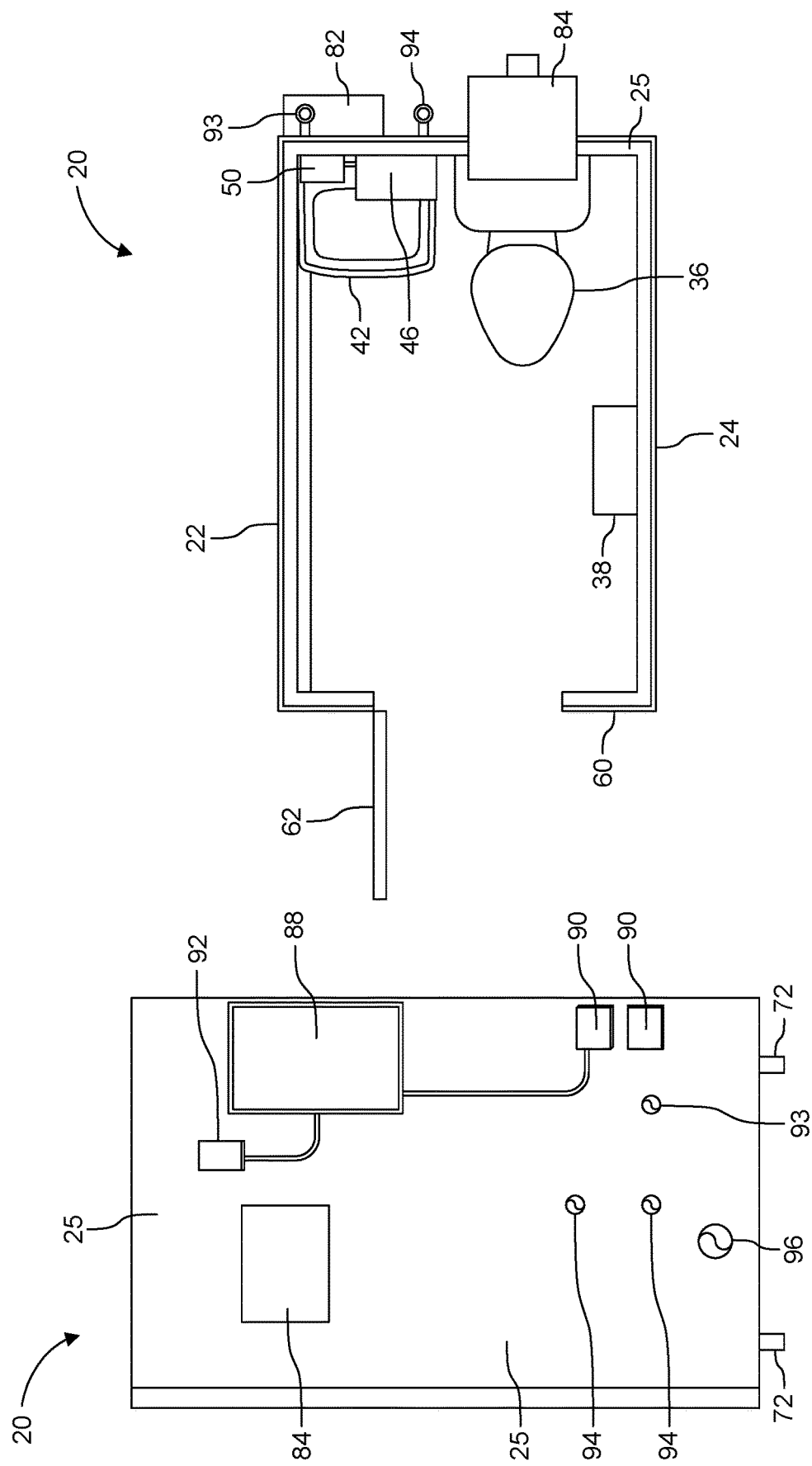

TEMPORARY RESTROOM AND WELLNESS POD

CROSS-REFERENCE TO RELATED APPLICATIONS

This application claims the benefit of U.S. Provisional Patent Application No. 62/947,728, filed Dec. 13, 2019, entitled, "CONSTRUCTION SITE TEMPORARY RESTROOM AND WELLNESS POD," the entirety of which is hereby incorporated by reference into the present application.

TECHNICAL FIELD

This application relates generally to the field of wellness hubs. More specifically, the application relates to a restroom that is temporary and connects directly to sanitization, electrical and domestic water systems in a site.

BACKGROUND

Many sites, such as construction sites or mining sites lack permanent restroom facilities, and workers must therefore use temporary restrooms positioned onsite. The typical portable restroom that one sees in parks and public spaces includes a septic tank to collect the waste from the toilet. For sanitary and health reasons, and because such a tank is not connected to the city sewage system, a typical portable restroom installed on a construction site must be drained and sanitized on a regular basis. This can be challenging, if not impossible, on some sites, such as high-rise buildings, due to the tight spaces, high elevation of the construction site, and the construction activity itself. Additionally, the septic tank in these portable restrooms is heavy when filled, and the overall size of such temporary restrooms can be quite large. Therefore, such restrooms often cannot be safely lifted to higher floors of a building under construction and cannot be easily moved between floors, cleaned, or emptied. On a mining site, such restrooms cannot be easily moved from the top of a site to the bottom or vice versa, or up or down a mining shaft.

As a result of these challenges of conventional portable restrooms, on some sites, workers must descend all the way to the ground floor anytime they need to use the restroom. On other sites, a small, portable toilet, such as the toilet 10 pictured in FIG. 1, may be used. This toilet 10 includes an outer plastic shell 11, a plastic door 12, a seated commode 13, a waste receptacle 14, a toilet tissue dispenser 15, a hand sanitizer dispenser 16, wheels 17 to provide rolling transport, and a crane handle 18 to allow the toilet 10 to be hoisted by a crane. Not pictured in FIG. 1 is a horizontal, slit-like opening at approximately mid-height along the back wall of the toilet 10, which acts as a urinal and empties into the waste receptacle 14. Although compact, this type of portable toilet 10 has a number of drawbacks. First, it affords almost no privacy to the user. A man using the urinal on the back of the toilet 10 must stand out in the open with no privacy, and a man or woman sitting on the seated commode 13 with the door 12 closed will still have his or her head exposed over the top of the toilet 10. This type of exposure while using the bathroom is not only potentially embarrassing, but it also leaves the user completely exposed to the elements. Construction sites can be extremely hot or extremely cold, depending on location and time of year, and the type of toilet 10 pictured in FIG. 1 does nothing to combat these extreme temperatures.

Additionally, maintaining proper sanitation while using the portable toilet 10 can be very challenging. With the COVID-19 pandemic and its aftermath, this issue is more important than ever. Although such a portable toilet 10 may include a hand sanitizer dispenser 16, it does not provide clean running water to wash one's hands. Also, like the larger portable toilets described above, the toilet 10 includes a waste receptacle 14, which may make it difficult to transport, empty and clean the toilet 10 in a sanitary manner, especially when it is positioned on a higher floor in a construction site. Currently, there are no better alternatives for temporary restrooms on construction sites. Workers must either descend to the ground floor, where better facilities are sometimes available, or avail themselves of a rudimentary, exposed, unsanitary toilet, such as the one illustrated in FIG. 1.

Therefore, it would be advantageous to have improved temporary restroom facilities for sites such as construction sites or mining sites, and potentially for other uses as well. It would desirable, for example, to have a temporary restroom that is sanitary, private and comfortable to use, while still being easily moveable through narrow hallways and other tight spaces on a construction site. Ideally, the restroom would also be capable of being safely lifted and moved between floors of a site with a hoist or crane, without risk of breaking or spilling hazardous contents on the worksite. Further it would be advantageous if the restroom is temporary and connects directly to sanitization, electrical and domestic water systems in a site. At least some of these objectives are addressed in this application.

BRIEF SUMMARY

A temporary restroom for use on sites and possibly other locations is described herein. Unlike the toilet 10 shown in FIG. 1, the temporary restroom described herein includes four walls, a floor, a ceiling and a door, to provide a fully enclosed space. The restroom structure includes a frame made up of multiple support members, typically but not necessarily made of metal, and at least one panel covering each wall of the frame. The frame provides the restroom with sufficient structural integrity to allow it to be lifted to high floors on a construction site, using a hoist and/or a crane. The temporary restroom also includes wheels on its bottom surface, to allow it to be wheeled around on the site. Different embodiments of the temporary restroom include different features, but all embodiments include a toilet, heating, ventilation, and air conditioning (HVAC), and running hot water via connection(s) to plumbing at the site, which may be temporary plumbing. Additional embodiments and features are described further below.

The temporary restrooms described herein may sometimes be referred to as "pods," and their method of construction may be generally referred to as "pod construction." The term "pod" is generally used to convey the fact that the temporary restrooms are designed so that they can be stand-alone unit that connect directly to sanitization and domestic water systems in a high-rise construction site. Unlike currently available and previously described temporary restrooms, the restrooms described herein do not include septic tanks, any other form of waste collection receptacles, or sources of water. Instead, the pod restrooms described herein include connections for connecting the pods with temporary or permanent plumbing on a construction site or other worksite. As the building is erected, the water, electric and sanitation pipes (referred to sometimes as "sanitation risers") are also installed. The pod capitalizes on these systems and taps into them as the building is constructed upwards. In some embodiments, each individual pod includes connection features that allow it to be attached to another pod to form a multi-room restroom and/or wellness facility. The connection features may reside, for example, on sidewalls of the pods. "Temporary," as used herein, means not permanently affixed to a property.

In some embodiments, the pod structure itself has a translucent ceiling, to provide natural lighting. The pod is sized and constructed such that it can be hoisted or lifted via a crane up into a building as it is being erected. The pod can also be easily removed from the site and transferred to another site for the same function. Thus, the temporary restrooms described in this application provide for easy mobility and require no sewage maintenance. Other aspects, in various embodiments, include natural lighting, running hot water, HVAC, sanitation devices, fully enclosed privacy, and installation features for a construction environment. In addition, the modularity of the pod allows for customized systems of multiple bathrooms and/or other types of rooms, based on the needs of a particular construction project.

In one aspect of the present disclosure, a temporary restroom includes an enclosure, which in turn includes: a front wall; a back wall; two sidewalls; a floor; a ceiling; and a door on the front wall. The front wall, the back wall, the two sidewalls, the floor and the ceiling each include multiple support members, where the multiple support members together form a frame configured so that the temporary restroom can be lifted off the ground with at least one of a hoist or a crane, and at least one panel covering the multiple metal support members. The temporary restroom also includes a toilet coupled with the back wall and a waste drainage pipe, a sink coupled with the back wall, a water pipe and a waste water drainage pipe, a water heater coupled with the back wall and the water pipe, a heating, ventilation and air-conditioning (HVAC) unit coupled with the back wall or one of the two sidewalls, and multiple wheels on the bottom of the temporary restroom.

The temporary restroom may also include one or more optional additional features, such as but not limited to a toilet paper dispenser, a sanitizer dispenser for dispensing soap and/or hand sanitizer, a hand drier, and a light. In some embodiments, the panel (or panels) covering the ceiling of the enclosure is at least partially translucent, thus allowing natural light to enter the enclosure. In some embodiments, the temporary restroom may further include an ultraviolet light and a motion sensor configured to detect motion of a user of the temporary restroom. In such embodiments, the ultraviolet light is configured to turn on automatically and remain illuminated for a preset amount of time when the motion sensor detects that no user is in the temporary restroom.

In some embodiments, the back wall of the temporary restroom may include at least one inner panel and at least one outer panel. The inner panel and the outer panel form a space in which one or more features of the temporary restroom may be housed. For example, a water heater may be located inside the space between the inner panel and the outer panel. The space may also house a common drainage pipe for receiving the waste drainage pipe and the waste water drainage pipe and connecting to a sewage pipe of a building under construction, an electrical panel, and/or a power connector for connecting the HVAC unit with an external source of electrical power. The temporary restroom may also include at least one handle on an outside surface for facilitating rolling the temporary restroom using the wheels. In some embodiments no features inside the temporary restroom touch the floor, thus facilitating cleaning of the floor.

In another aspect of the present disclosure, a temporary restroom includes an enclosure, formed by: a front wall; a back wall; two sidewalls; a floor; a ceiling; and a door. The enclosure is formed by a frame including multiple support members. The temporary restroom also includes a toilet coupled with a waste drainage pipe, a sink coupled with a water pipe and a waste water drainage pipe, and multiple connections for connecting the waste drainage pipe and the waste drainage pipe to waste plumbing, connecting the water pipe to water plumbing, and connecting the temporary restroom to a source of electric power. The temporary restroom does not include a waste storage tank or a built-in source of water.

Optionally, the temporary restroom may also include a water heater coupled with the water pipe, a heating, ventilation and air-conditioning (HVAC) unit, and/or multiple wheels on a bottom of the temporary restroom. Further optional features include a toilet paper dispenser, a sanitizer dispenser for dispensing soap and/or hand sanitizer, a hand drier, and/or a light. Panels may be used to cover the support members of the frame, and in some embodiments, at least one panel covering the ceiling of the enclosure is at least partially translucent. The multiple connections of the temporary restroom may include a common drainage pipe with a first end for connecting to the waste drainage pipe and the waste water drainage pipe and a second end for connecting to the waste plumbing and an electrical outlet, either or both of which may be attached to the back wall.

In another aspect of the present disclosure, a temporary restroom system may include multiple temporary restroom units, each of the temporary restroom units including a toilet, a front wall, a back wall, two sidewalls, a floor, a ceiling, a door, and connection members on an outer surface of each of the two sidewalls, for connecting the temporary restroom units together. The system may also include multiple attachment members for attaching the connection members of one of the temporary restroom units with the connection members of another of the temporary restroom units. Notably, none of the temporary restroom units includes a waste storage tank or a built-in source of water.

Optionally, some or all of the temporary restroom units may further include at least one additional feature selected from the group consisting of a sink, a water heater, a heating, ventilation and air-conditioning (HVAC) unit, multiple wheels on a bottom of the temporary restroom unit, a toilet paper dispenser, a sanitizer dispenser for dispensing at least one of soap or hand sanitizer, a hand drier, and a light.

In some embodiments, the system includes a break room unit that does not include a toilet but does include compatible connection members to connect the break room unit with at least one of the multiple temporary restroom units. For example, the break room unit may include a sink, and the system may include a common waste pipe connection for connecting a waste pipe from at least one of the temporary restroom units and a waste water pipe from the sink with waste plumbing. In some embodiments, the temporary restroom units, when attached to one another, are aligned side-by-side in a row, and the break room unit is attached to a free side of one of the temporary restroom units at one end of the row. Each of the temporary restroom units may be sized and configured to be lifted to an above-ground-level floor of a construction site with at least one of a crane or a hoist These and other aspects and embodiments are described in further detail below, in reference to the attached drawing figures.

BRIEF DESCRIPTION OF THE DRAWINGS

FIG. 8 is a front plan view of the temporary restroom of FIGS. 6-7, showing the interior and back wall of the restroom;

FIG. 9 is a side plan view of the temporary restroom of FIGS. 6-8, showing the interior and one side wall of the restroom;

FIG. 10 is a rear exterior view of the temporary restroom of FIGS. 6-9;

FIG. 11 is a top plan view of the temporary restroom of FIGS. 6-10, with the top removed to show the inside of the restroom;

DETAILED DESCRIPTION

As mentioned above, this disclosure describes a temporary restroom for construction sites or other locations, such as a mining site, other worksite, large public events such as concerts or running races, or any other suitable uses or locations. Although the focus of this disclosure is on a temporary restroom for construction sites, such as high-rise building, and some embodiments are designed specifically to be lifted to the second floor or higher floors of a building, any of the embodiments described herein may be used, or adapted for use, in other settings.

One notable advantage of the temporary restroom described herein is that it does not include a built-in septic tank or any other tank or receptacle for containing waste or water. Therefore, the temporary restroom unit (or "pod") can more easily and safely be transported and moved from floor to floor of a building under construction, without fear of waste spillage and contamination. It is also lighter than temporary restrooms with full septic tanks, and does not require emptying or smell like accumulated human waste. Embodiments described herein often also include a sink, but the example embodiments of a temporary restroom herein do not include built-in water supplies or drainage tanks for waste water. The temporary restroom also often includes at least one electrically powered feature, such as an HVAC system, a water heater and/or lighting, but again, the temporary restroom does not include built-in power supplies. Instead, each of the embodiments described herein includes connections for coupling with (1) a sewage pipe and sewage system and optionally (2) a water pipe/water supply and/or (3) a source of electricity. On construction sites, these connections may be made to temporary plumbing ("risers") or permanent plumbing and a temporary or permanent source of electricity for the building under construction. The temporary restroom can be moved and lifted easily by a crane and/or hoist and may be wheeled or otherwise moved along a particular floor of a building and then connected with the building's plumbing and electricity. This modularity and lack of septic and water tanks helps provide portability and maintain sanitation of the temporary restroom described in this application.

Figure 2:
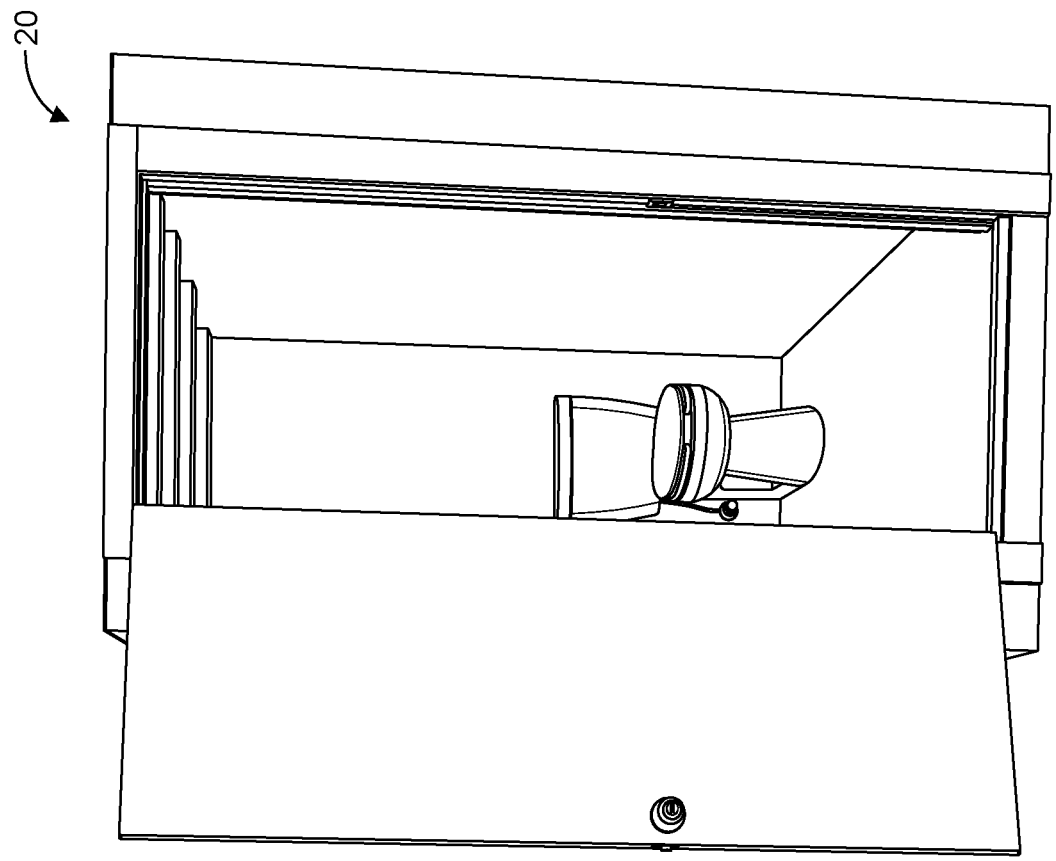
FIG. 2 is a front view of a temporary restroom, according to one embodiment.
Figure 1:
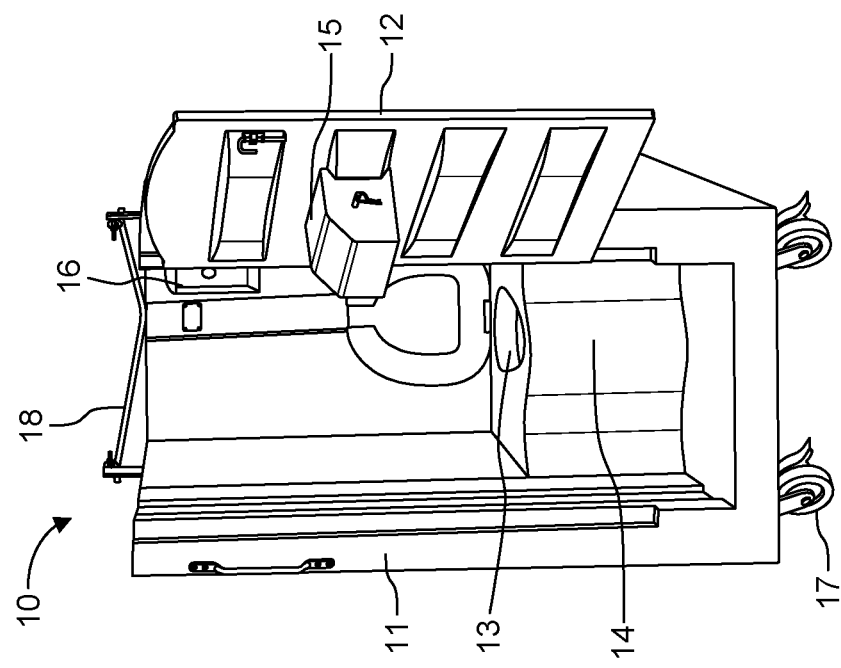
FIG. 1 is a front view of a prior art portable toilet for construction sites.

Referring now to FIG. 2, a simplified perspective view of a temporary restroom 20 for construction sites is provided. FIG. 2 illustrates the temporary restroom 20 with many of its internal features removed, simply to show that the temporary restroom 20 is a fully enclosed structure, with four walls, a ceiling, a floor, and a door. This is in contrast to the prior art construction site toilet 10 of FIG. 1, with its open top that exposes the user to anyone within sight and to the elements. Many other aspects and features of the temporary restroom 20 are described further below, in reference to more detailed drawings.

Figure 3:
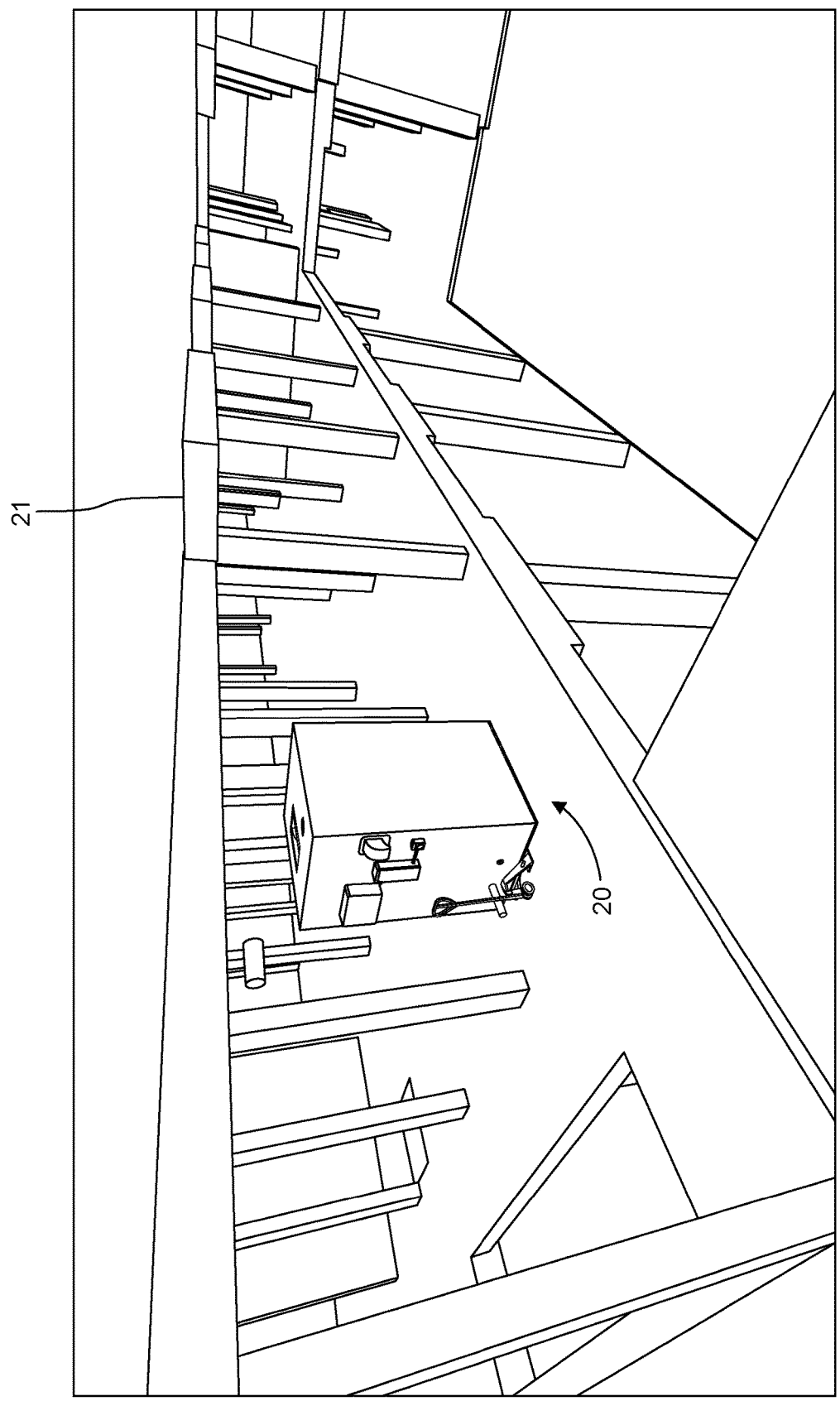
FIG. 3 is a perspective view of a temporary restroom, according to one embodiment, shown with a lift device on the second floor of a building under construction.

FIG. 3 shows the temporary restroom 20 from a rear perspective view on the second floor of a construction site 21. As mentioned above, the temporary restroom 20 of this application is designed to be lifted via hoist and/or crane to floors of a construction site above the ground floor and then wheeled to a desired location on a given floor. In some embodiments, as illustrated in FIG. 3, the temporary restroom 20 may be moved using a lift. Additionally or alternatively, the temporary restroom 20 may have wheels on its bottom surface and optionally one or more handles for pushing and/or pulling the temporary restroom 20 along a floor. In various embodiments, the temporary restroom 20 may be used on a lower floor of a building and then, as the building grows higher, the temporary restroom 20 may be moved by hoist or crane to a higher floor. This may be repeated as many times as desired. Without a built-in septic tank or water tank, the temporary restroom 20 may be moved from floor to floor more safely and easily than previously available portable toilets.

Figure 4:
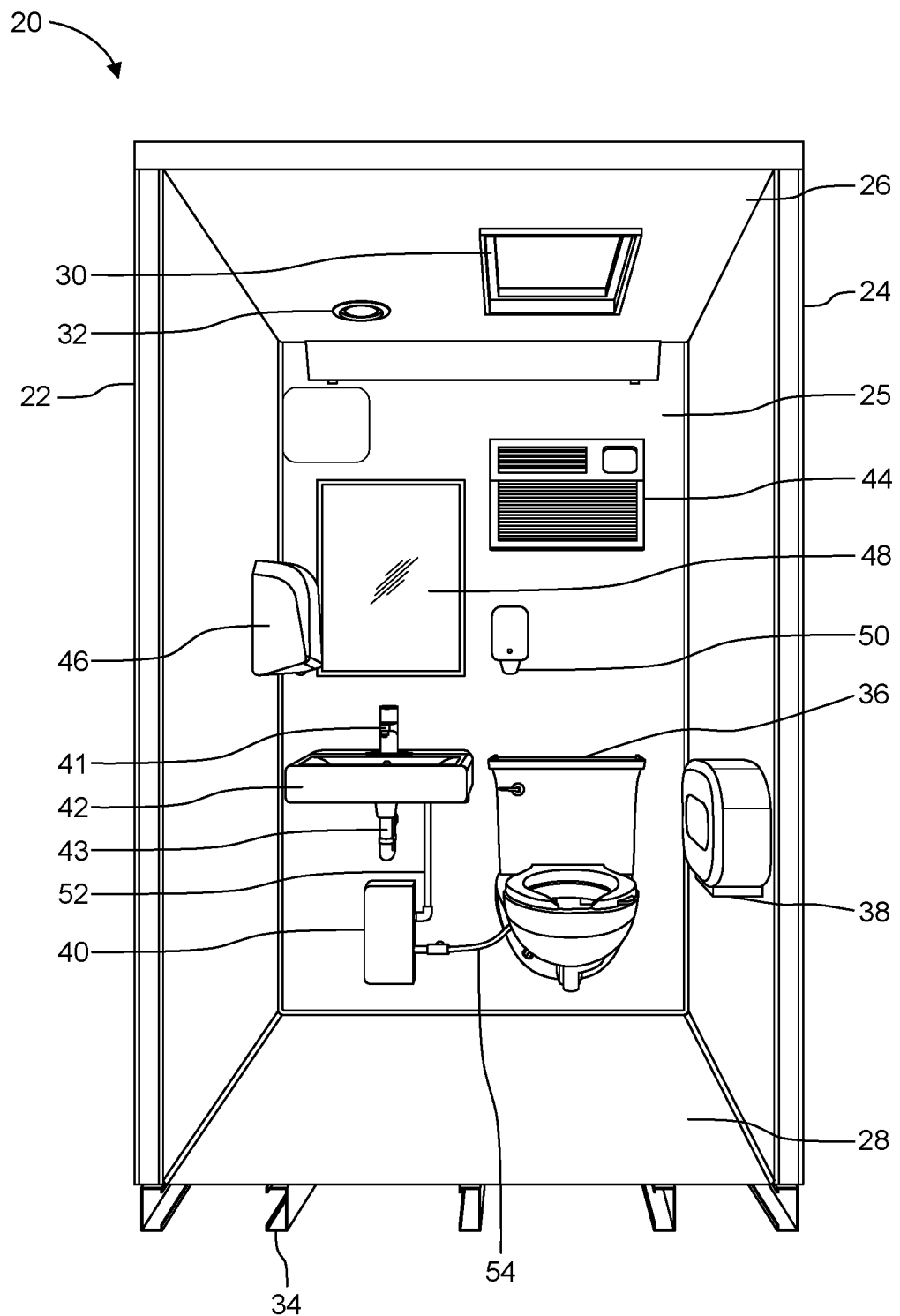
FIG. 4 is a front view of a temporary restroom, with the front wall removed to show the interior of the restroom, according to one embodiment.

Referring now to FIG. 4, a front view of one embodiment of the temporary restroom 20 is illustrated, with a front wall 60 and a door 62 removed (see FIG. 5B for both), to better show the inside of the temporary restroom 20 (also referred to herein as "the enclosure" or "the inner enclosed space"). This combination and configuration of the temporary restroom 20 is merely one example, and in any given embodiment additional features may be provided and/or illustrated features may be moved to a different location, altered, swapped out for a different feature, or removed altogether. In this embodiment, the temporary restroom 20 includes a left sidewall 22, a right sidewall 24, a back wall 25, a ceiling 26, a floor 28, and (as shown in FIG. 5) the front wall 60 and the door 62. Each of the left sidewall 22, the right sidewall 24, the back wall 25, the ceiling 26, the floor 28, and the front wall 60 includes multiple support members 34 (or "support beams") and at least one panel disposed over the support members 34 to form a wall. All of the support members 34 for all of the walls 22, 24, 25, 60, the ceiling 26 and the floor 28, when attached together, form a frame (or "skeleton") of the temporary restroom 20. The frame, the door 62 and the panels, which will be described further below, form the completely enclosed inside space of the temporary restroom 20.

In the embodiment of FIG. 4, the enclosure of the temporary restroom 20 includes a toilet 36, which is attached directly to the back wall 25 and "floats" above the floor 28. The toilet 36 is connected to a toilet water inlet pipe 54, which connects to a common water inlet, which in this embodiment is covered by a cover 40. The enclosure also houses a sink 42 with a faucet 41, a sink water inlet pipe 52, and a waste water pipe 43. The common water inlet may simply include a pipe and a cover 40. The pipe of the common water inlet (not visible, because located behind the cover 40) may connect at one end to the toilet water inlet pipe 54 and the sink water inlet pipe 52 and at another end to a temporary or permanent water pipe connected to the building's plumbing system. The enclosed inside space of the temporary restroom 20 may also include a toilet paper dispenser 38, a hand sanitizer dispenser 50, an HVAC unit 44, a hand drier 46, a mirror 48, one or more lights 32 and one or more skylights 30.

As discussed above, one significant feature of the temporary restroom 20 is that it does not include a septic tank for collecting waste from the toilet 36 or the sink 42, nor does it include a built-in water source for providing water to the sink 42 or a built-in source of electricity. As discussed above, conventional portable toilets typically include a septic tank (or other built-in waste collection receptacle), which requires frequent emptying and is usually chemically induced, smelly and potentially unsanitary. The temporary restroom 20 described herein does not include a waste tank, a source of water, or a source of electricity, but instead includes connections for sanitary waste, potable water and electricity, which allow the temporary restroom 20 to be connected to temporary and/or permanent waste and water plumbing and a source of electrical energy that are available at the construction site. Eliminating the septic/waste tank and providing water and electrically powered features, without built-in sources of water or electricity, allow the temporary restroom 20 to be portable, sanitary, and adaptable to many different types, sizes and configurations of construction sites (or other sites, such as mining sites, large events or other worksites).

In some embodiments, at least the body and tank of the toilet 36 are constructed of porcelain, thus looking and feeling like a toilet that one would find in a home or other permanent structure. The toilet 36 is attached to the back wall 25 and floats above the floor 28, to make cleaning the floor with a hose, mop or any other cleaning tool(s) easier. Due to the weight of a porcelain toilet 36, the toilet 36 is attached directly to at least one, and preferably two or more, of the metal support members 34 that form the frame of the back wall 25. The toilet 36 may be attached to the support members 34 via bolts, grommets, screws and/or any other attachment devices or combinations thereof. The basin of the sink 42 may also be porcelain and may be attached in a similar way to the support members 34 of the back wall 25.

The hand drier 46 may be an electric/air hand drier, for example. Alternatively, the hand drier 46 may be a paper towel dispenser, revolving cloth towel dispenser or any other type of hand drying device or dispenser. An electric hand drier 46 might be more sanitary and less environmentally wasteful than other options. In various embodiments, the hand drier 46 may be placed on the left sidewall 22, as shown, or alternatively on the right sidewall 24 or the back wall 25. In some embodiments, the hand drier 46 may be positioned over the sink 42 to facilitate maintaining cleanliness of the enclosure of the temporary restroom 20, since water from the users' hands will drip into the sink as the users dry their hands with the hand drier 46. The hand sanitizer dispenser 50 may be configured to dispense soap, hand sanitizer, or both, and it may be any suitable known soap or hand sanitizer dispenser and may similarly be placed over the sink 42. The toilet paper dispenser 38 may also be any suitable known dispenser and is attached to the right wall 24 or one of the other walls in alternative embodiments. The attachment of all the inside features of the temporary restroom 20 directly to the walls, without having any features resting on the floor 28, again allows for easy cleaning of the floor 28 of the temporary restroom 20, for example by simply hosing the floor 28 down with a hose.

The temporary restroom 20 also includes a heating, ventilation and air-conditioning (HVAC) unit 44, which may be installed on any of the walls but may be most conveniently attached to the back wall 25. The HVAC unit 44 may be any standard or custom HVAC system, as appropriate. The inclusion of the HVAC unit 44 in the temporary restroom 20 addresses the issue mentioned above of hot and cold temperatures on construction sites, and it also helps pressurize the inside enclosure of the temporary restroom 20, to reduce waste smells and keep the air in the enclosure clean. In some embodiments, the HVAC unit 44 includes an air filtration system, to provide for further air purification inside the enclosure of the temporary restroom 20.

One or more lights 32 may be embedded in and/or attached to the ceiling 26 and/or any of the walls of the temporary restroom 20. The light(s) 32 may be any suitable type of light, such as LED, incandescent, halogen, fluorescent or the like. In some embodiments, the lights(s) 32 may turn on and off automatically, based on a motion sensor located on one of the walls 60, 22, 24, 25 of the temporary restroom 20. This automatic on/off feature allows the users of the temporary restroom 20 to enjoy a lighted enclosure without having to touch a light switch with their hands, thus helping maintain a more sanitary enclosure and worksite. In some embodiments, the light(s) 32 may include one or more ultraviolet C (UV-C) lights. The UV-C lights may emit light at a wavelength configured to kill germs, viruses, bacteria and/or the like. For example, UV-C light has been shown to effectively kill the COVID-19 virus. In one embodiment, one or more UV-C lights inside the temporary restroom 20 may be connected to a motion sensor that activates the lights when no motion is detected (in other words, the opposite of the way most motion sensor lighting works). The UV-C lights inside the temporary restroom 20 thus illuminate after a user leaves the temporary restroom 20 (and no motion is detected), and they remain on for a period of time (e.g., 5-15 minutes) designed to kill a majority of any virus or other germs that might have been left behind by the user. The UV-C light then turns off and does not turn on again until the next user exits the temporary restroom 20. This configuration of one or more UV-C lights helps keep the enclosure clean and germ free, without exposing the users of the temporary restroom 20 to potentially harmful UV-C light. In some embodiments, the lights 32 in the temporary restroom 20 may include a combination of illuminating lighting for the user and UV-C lighting for sanitation purposes.

Another feature of the temporary restroom 20 is that natural light is provided, via one or more skylights 30. The skylights can have any suitable size, shape and number, according to various embodiments. In alternative embodiments, the entire panel (or panels) attached to the support members to form the ceiling 26 is at least partially translucent, so the entire ceiling 26 allows natural light to enter the enclosure of the temporary restroom 20. In other words, the ceiling 26 itself is one big skylight. In such embodiments, the light(s) 32 may alternatively be positioned on a sidewall 22, 24 or the back wall 25. Alternatively, if the translucent ceiling 26 allows in sufficient light, it might be unnecessary to have any electric lights 32 in the temporary restroom 20.

Figure 5A:
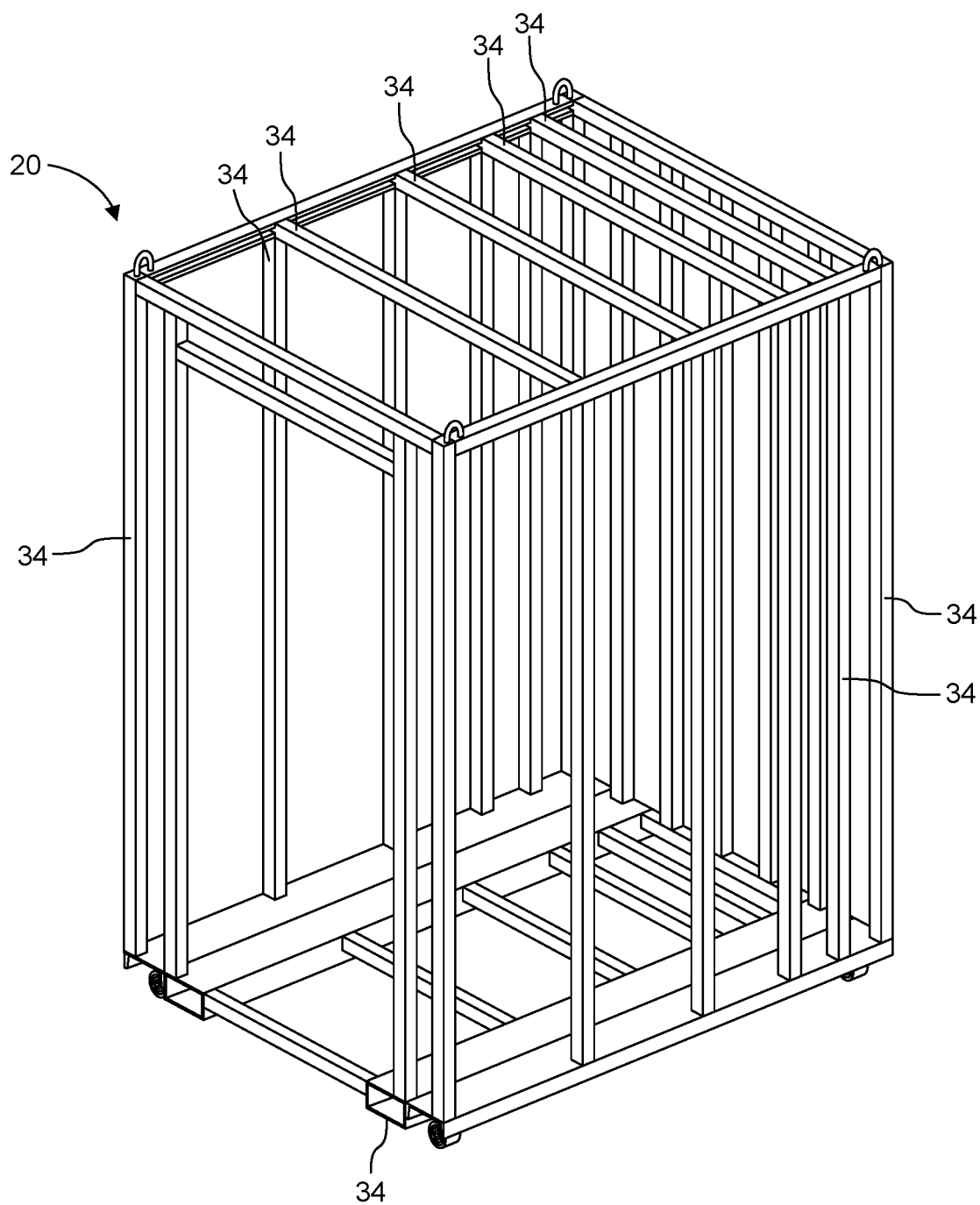
FIG. 5A is a top/front perspective view of a frame of a temporary restroom, made up of multiple support members, according to one embodiment.
Figure 5B:
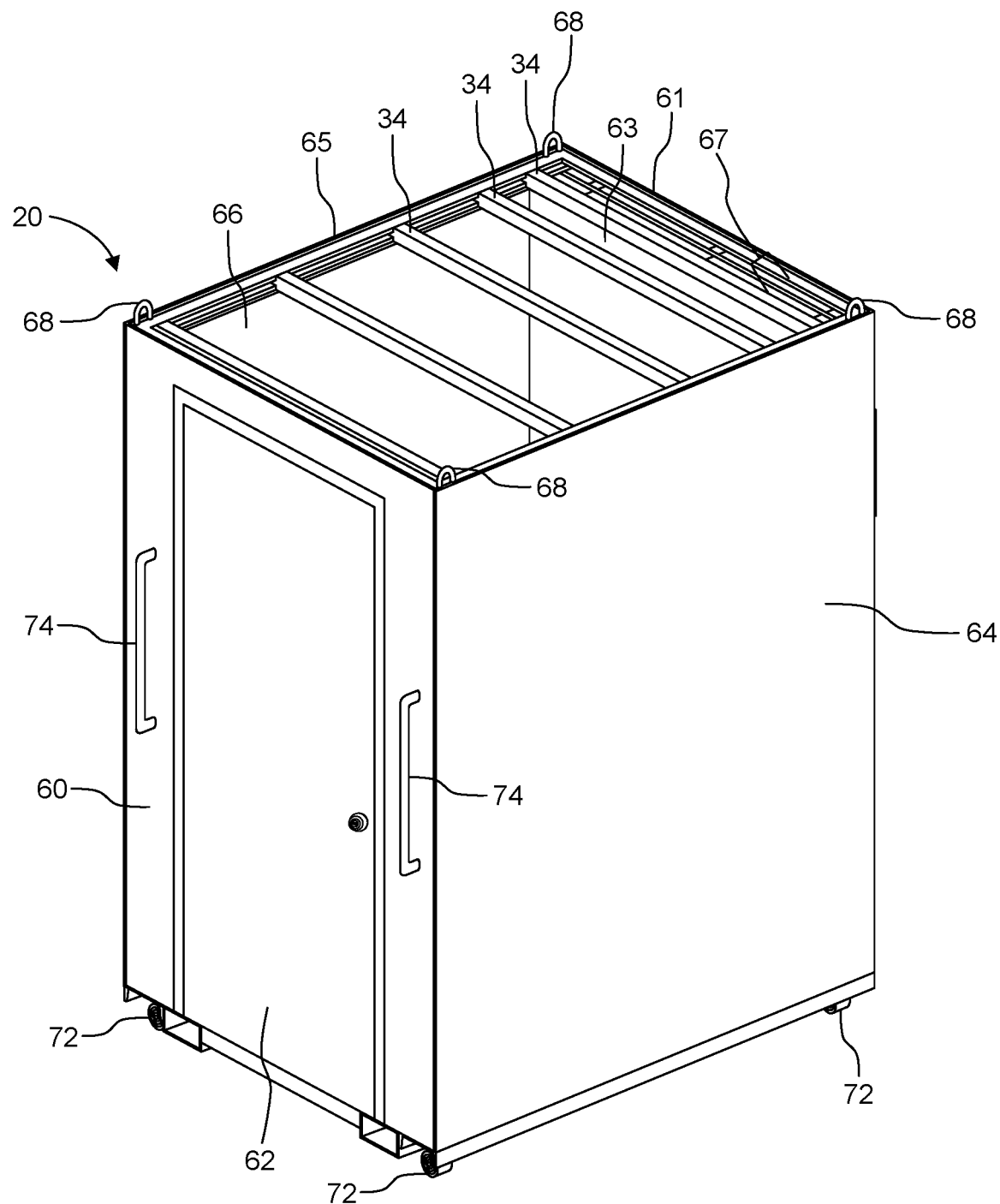
FIG. 5B is a top/front perspective view of the temporary restroom of FIG. 5A, with walls attached to the support members other than on the roof/ceiling.

Referring now to FIG. 5A, the frame of the temporary restroom 20 is illustrated, according to one embodiment. As discussed previously, the frame is made up of multiple support members 34, making up the walls, floor and ceiling of the temporary restroom 20. In some embodiments, the support members 34 are made of metal, such as steel or aluminum. (The support members 34 in some embodiments may be referred to as "steel studs.") They may be attached to one another by any suitable attachment devices and construction techniques. The support members 34 and the frame as a whole provide structural integrity to the temporary restroom 20, which allows the temporary restroom 20 to be lifted to high floors of a construction site via a hoist and/or crane. Additionally, heavier items inside the enclosure of the temporary restroom 20, such as the porcelain toilet 36 and the porcelain sink 42, may be attached directly to support members 34 with grommets and/or any other attachment members, to help provide a sturdy temporary restroom 20.

FIG. 5B shows the temporary restroom 20 of FIG. 5A, with panels attached to most of the support members 34, other than on the ceiling, to form walls. FIG. 5B also shows the door 62 of the restroom 20. Each wall of the temporary restroom 20, as well as the ceiling and the floor, is made up of multiple support members 34 and at least one panel of material covering the support members 34. The panels may be made of any suitable material, such as but not limited to drywall, wood or fiberglass. In some embodiments, the panels are fiberglass reinforced panels (FRP), and FRP may be generally used to describe the panels herein. In some embodiments, each wall may include two panels—one on the outside of the support members 34 and one on the inside. For example, FIG. 5A shows a front wall outer panel 60, a right sidewall outer panel 64, the edge of a left sidewall outer panel 65, a left sidewall inner panel 66, the edge of a back wall outer panel 61, and a back wall inner panel 63. The back wall inner panel 63 and back wall outer panel 61 define a space 67 that can contain components such as a common drainage pipe. In various embodiments, multiple numbers, shapes and sizes of panels may be used to construct any one or more of the walls. Covering the support members 34 on both sides with panels makes the overall appearance of the temporary restroom 20 more like that of a permanent or home restroom.

The ceiling panel, which is not shown in FIG. 5B, may be made of a translucent material to allow natural light to enter the enclosure of the temporary restroom 20 from above. In the case of the ceiling, one panel may simply be used, leaving the bottom or top surface of the ceiling support members 34 exposed. Alternatively, two translucent panels may be used. The translucent panel(s) may be made of any suitable material, such as any plastic, polymer, glass, fiberglass, or the like. In other embodiments, such as the one illustrated in FIG. 4, opaque panel(s) may be used to form the ceiling 26, and one or more skylights may be cut into the panel(s). The floor of the temporary restroom 20, which also is not visible in FIG. 5B, may be made of one or more panels placed on the top side of the floor support members 34, leaving the bottom surface of the floor support members exposed below. The floor panel(s) may be made of a durable material that is easy to clean, such as sheet vinyl, sheet metal, stainless steel, aluminum, another type of metal, or a polymeric material.

In some embodiments, the temporary restroom 20 may also include multiple crane attachment members 68, such as the semi-circular loops shown in the upper four corners of the restroom in FIG. 5B. The crane attachment members 68 may be made of metal and may be attached directly to the support members 34 and extend through any top panel of the temporary restroom 20, to allow a cable to pass through the attachment members 68 and then attach to a crane. Placing the crane attachment members 68 at or near all four top corners of the temporary restroom 20 allows a crane and cable to lift the temporary restroom 20 via a symmetric attachment, thus helping ensure safe and non-destructive lifting. In alternative embodiments, the attachment members 68 may be positioned in other locations on the restroom and/or may differ in number. The attachment members 68 may be semicircular loops, as shown, or alternatively hooks, bolts, eyelets, or any other suitable type of fastening device.

Also shown in FIG. 5B are wheels 72 on the bottom of the temporary restroom 20 and two handles 74 on the front wall 60. (A fourth wheel 72 on the fourth corner of the bottom of the temporary restroom 20 and a fifth wheel 72 in the middle of the bottom are not visible). The wheels 72 and handles 74 are used to move the temporary restroom 20 onto and off of a hoist and to move the temporary restroom 20 to a desired location on a floor of a construction site. The handles 74 may be metal or any other suitable material and may be placed on one or multiple walls of the temporary restroom 20.

In an alternative embodiment to that shown in FIGS. 5A and 5B, each wall of the temporary restroom 20 may be made of a one-piece panel, rather than separate beams and panels attached to the beams. These one-piece panels may be made of any suitable plastic or polymer, for example, and each one-piece panel may be a single mold. In another alternative embodiment, the entire shell of the temporary restroom 20 may be one piece of material, such as plastic or polymer. In some embodiments, the entire shell may be a single mold.

Figure 7:
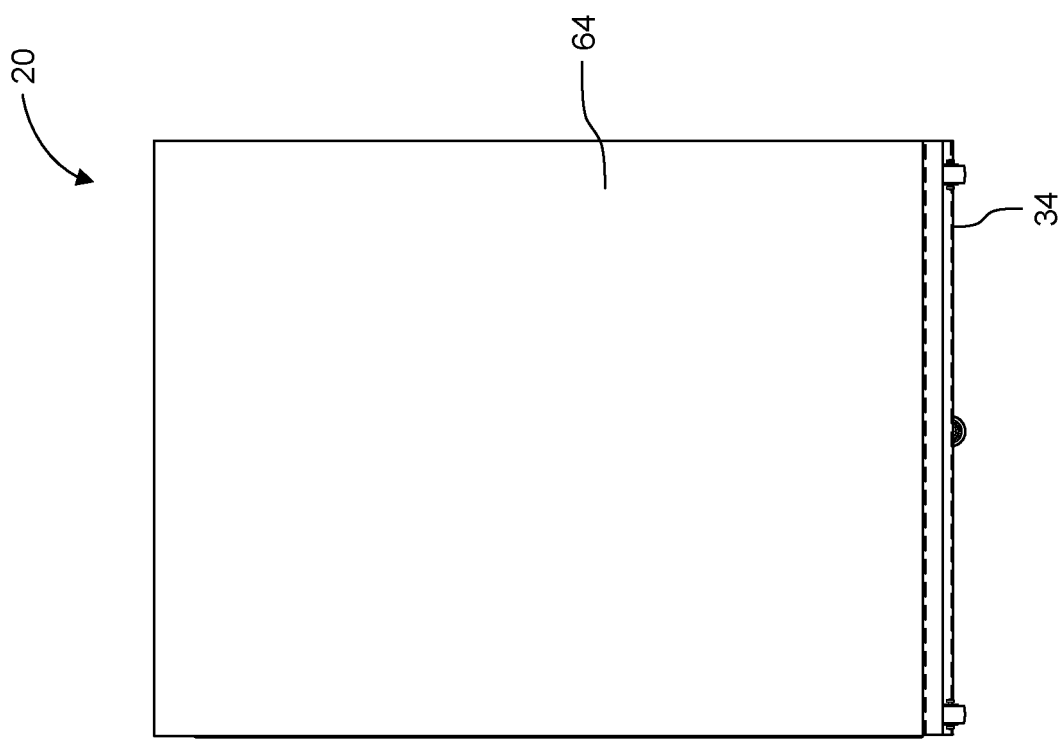
FIG. 7 is an exterior side view of the temporary restroom of FIG. 6.
Figure 6:
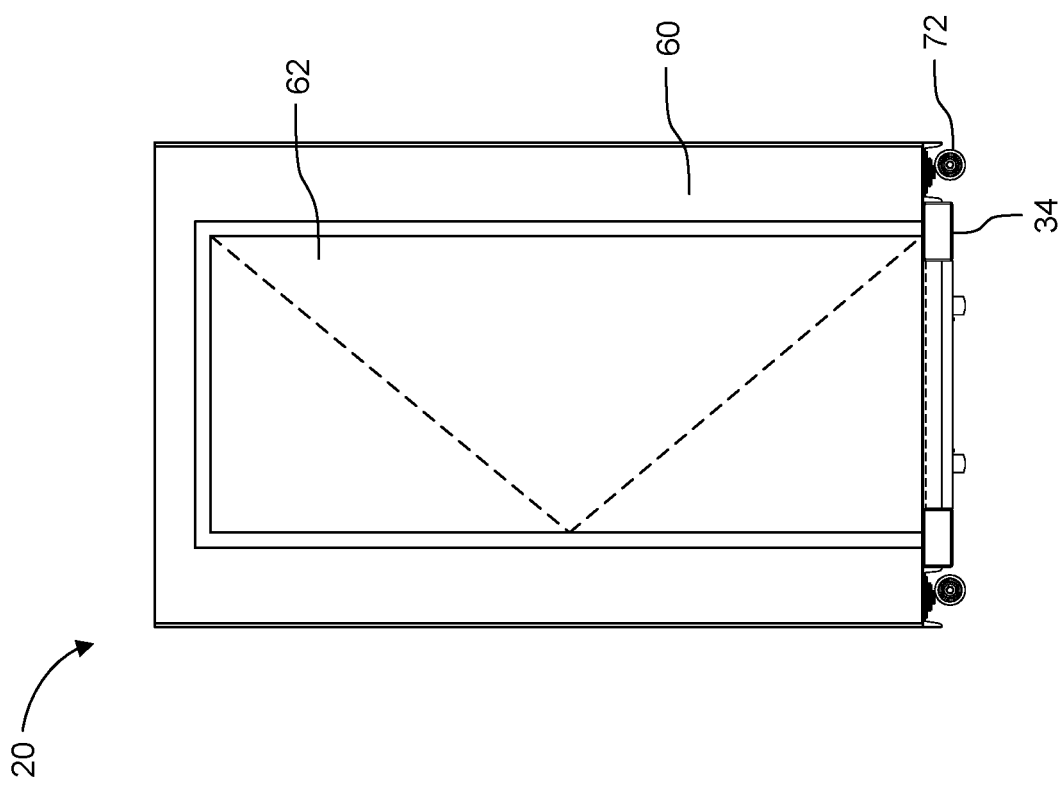
FIG. 6 is an exterior front view of a temporary restroom, with the door closed, according to one embodiment.

Referring now to FIGS. 6 and 7, outer front and right side views, respectively, of the temporary restroom 20 are provided. It may be highly advantageous to provide the temporary restroom 20 with specific dimensions, to allow it to be rolled through an open gate of a hoist. Although different hoists have different open gate heights, the temporary restroom 20 may be designed to fit through the smallest hoist gate opening height. For example, the outer dimensions of one embodiment of the restroom, including the wheels 72, may be: height 7'4.75"; width 4'8"; and depth 7'1.25". This is merely one example, however, and other embodiments may have different dimensions designed for other hoist sizes, hallways of a particular building site, or any other design specifications. In various alternative embodiments, for example, the dimensions of the restroom may be in the ranges of: height 6.5'-8'; width 4'-5'; and depth 6.5'-11'. Again, these ranges are only examples, and some embodiments of the temporary restroom might fall outside these ranges.

FIGS. 8 and 9 are inside front and inside right views, respectively, of the temporary restroom 20. The view in FIG. 9 is from the right side looking toward the left sidewall 22, with the toilet 36 not illustrated. The embodiment illustrated in FIGS. 8 and 9 has a different inside configuration than that of FIG. 4, but features that are common to both embodiments are given the same reference numbers. Only new or modified features will be described here. For example, the toilet 36, in this embodiment, extends to and is mounted on the floor 28. The electric hand drier 46 and sanitizer dispenser 50 are both attached to the back wall 25, over the sink 42. This embodiment of the temporary restroom 20 includes an electric baseboard heater 80 and a separate air-conditioning unit 84. A single-module water heater 82 is also shown, attached to the back wall 25. FIG. 9 shows a light switch 86 attached to the left sidewall 22, a 50W electric panel 88 and a waste water pipe connector 89 attached to the outer surface of the back wall 25. In any of the embodiments described herein, some the waste water pipe connector 89 and/or any connectors to the building's temporary or permanent sewage system, water system and/or electrical system may be "quick release" connectors that facilitate easy and quick attachment and release of the pipes and electrical wiring to the building's plumbing and electrical source.

One primary difference between the embodiment of FIGS. 8 and 9 and the embodiment of FIG. 4 is that the toilet 36 and the heater 80 are attached to the floor 28. This might be less ideal for ease of cleaning the floor 28, but in some cases this configuration might provide for greater stability and durability of the toilet 36, for example.

Referring now to FIG. 10, a rear view of the temporary restroom 20 of FIGS. 6-9 is illustrated. In many embodiments, many or all of the connectors of the temporary restroom 20, for connecting with temporary and/or permanent plumbing and electricity of a building construction site, are located on the back wall 25 of the temporary restroom 20. These connectors may be attached to an outer surface of the back wall 25 or may extend from inside the enclosure through the back wall 25. Other features of the temporary restroom 20 may also be attached to, or extend through, the back wall 25. In this embodiment, for example, the air conditioning unit 84, three 2" DIA plumbing connections 93, 94, and one 4" DIA plumbing connection 96 extend through the back wall 25. The plumbing connections 93, 94, 96 connect pipes of the toilet 36 and the sink 42 to the building's plumbing for supplying water to the temporary restroom 20 and removing waste. Again, in some embodiments, any or all of these connections 93, 94, 96 may have quick release functionality. Other features attached to the back wall 25 include, but are not limited to, two electrical outlets 90, an industrial fixture 92 and a 50W electrical panel 88.

FIG. 11 is a top view of the temporary restroom 20 of FIGS. 6-10, with the ceiling removed to better see the inside floor plan. The door 62, which may be made of any suitable material, is shown open. The air-conditioning unit 84, which may for example be a 5,000 BTU window-mounted air-conditioning unit, extends through the back wall. The plumbing connection 93, which provides water to the sink 42, is illustrated passing through the water heater 82. In one embodiment, the sink 42 may have a simple faucet that provides only warm water, thus eliminating the need for hot and cold faucets or adjustable faucets. Another 2" plumbing connection 94 directs waste water from the sink 42 to the waste water system of the building.

Figure 12:
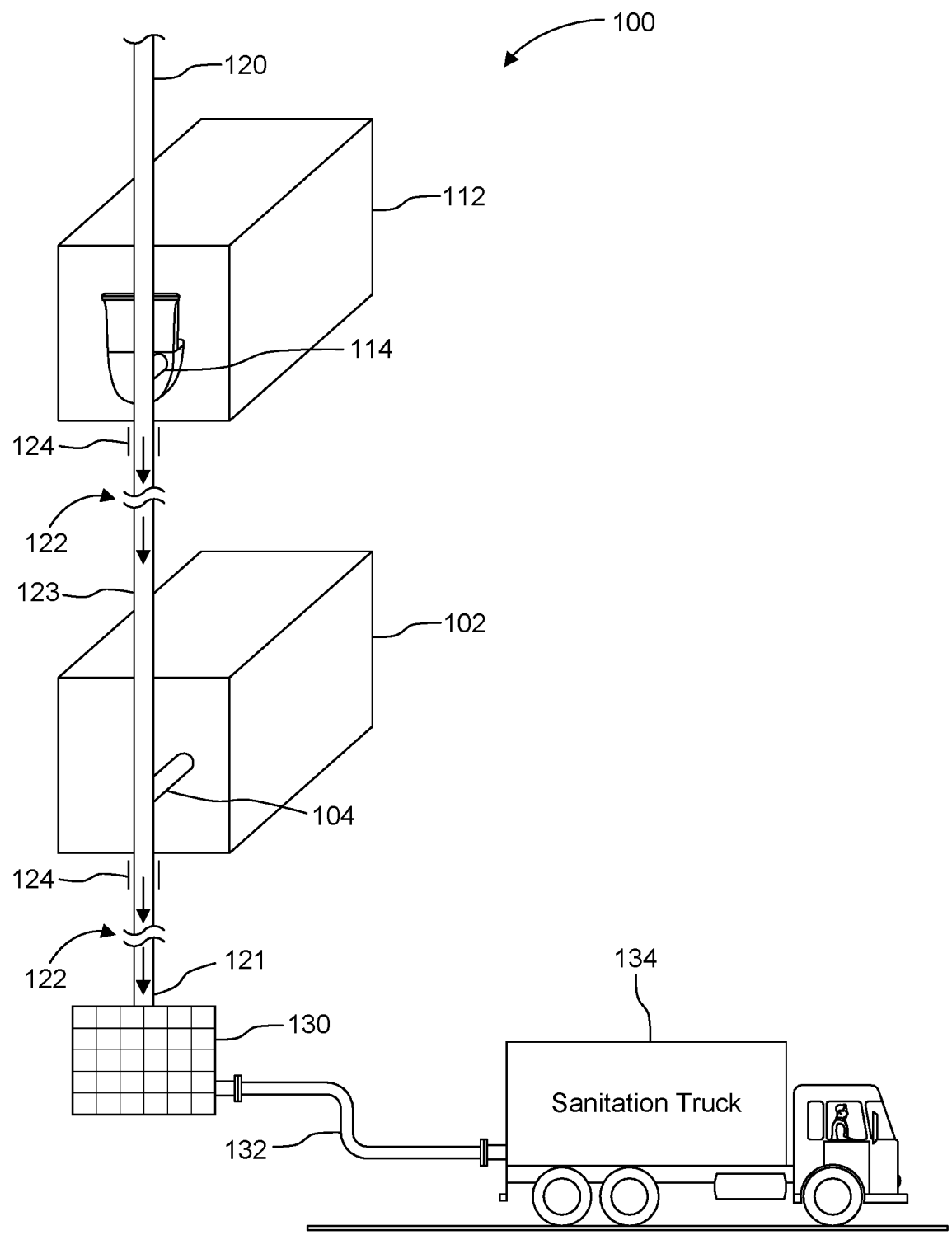
FIG. 12 is a perspective diagrammatic view of multiple temporary restroom facilities connected to a common plumbing system in a building, according to one embodiment.

Referring now to FIG. 12, a multiple-restroom system 100 for a high-rise construction site is illustrated in diagrammatic form. The actual high-rise is not shown in the illustration. Here, the system 100 includes a first temporary restroom 102 located on one floor of the site and a second temporary restroom 112 located on another floor of the site. On the ground floor 130 of the construction site is a central sewage system. Between the ground floor 130 and the first temporary restroom 102 there are intervening floors 122, and between the first temporary restroom 102 and the second temporary restroom 112 there are more intervening floors 122. The temporary restrooms 102, 112 may be placed on any floors, as desired. In some embodiments, for example the temporary restrooms 102, 112 may be placed every fourth floor, but this is merely one example. Each temporary restroom 102, 112 includes plumbing connections 104, 114, which have been described in more detail above. These connections 104, 114 connect the restrooms 102, 112 to a first end or portion 123 of a temporary "riser" 120, installed by the construction site plumber, or to other temporary or permanent plumbing common to the building. Each floor where a temporary restroom 102, 112 is located may include a sleeve 124 on the riser 120 for connecting the connections 104, 114 with the riser 120. Waste and waste water from the restrooms 102, 112 passes through a second end or portion 121 of the riser 120 to the common sewage system on the ground floor 130 and from there may be transported to a sanitation truck 134 via a pipe 132. Electrical connections to the restrooms 102, 112 may be simple connections of an electrical cable running from the building's electrical source to an outlet on each temporary restroom 102, 112, such as a marine connection.

According to various alternative embodiments, any number of temporary restrooms 102, 112 may be used at a given construction site, and they may be moved to different floors as often as desired. For example, one site might install five temporary restrooms 102, 112 on every fourth floor starting from the ground floor. As construction of the building continues and the focus of the construction moves higher and higher, temporary restrooms 102, 112 from the lower floors may be rotated up to higher floors. This may be done, for example, with the same five temporary restrooms 102, 112 until the building is completed. Since the temporary restrooms 102, 112 are easy to move, they can be transported to different floors and moved within a floor with relative ease. In some embodiments, for example, the temporary restrooms 102, 112 may located in the hoist unit of each floor, for easy access to the hoist and to connections to the riser. Each temporary restroom 102, 112 may also be delivered onto a "drawer" or lookout of a floor of a high-rise building and then moved via wheels and optional handles on the temporary restroom 102, 112 to the hoist unit.

Figure 13:
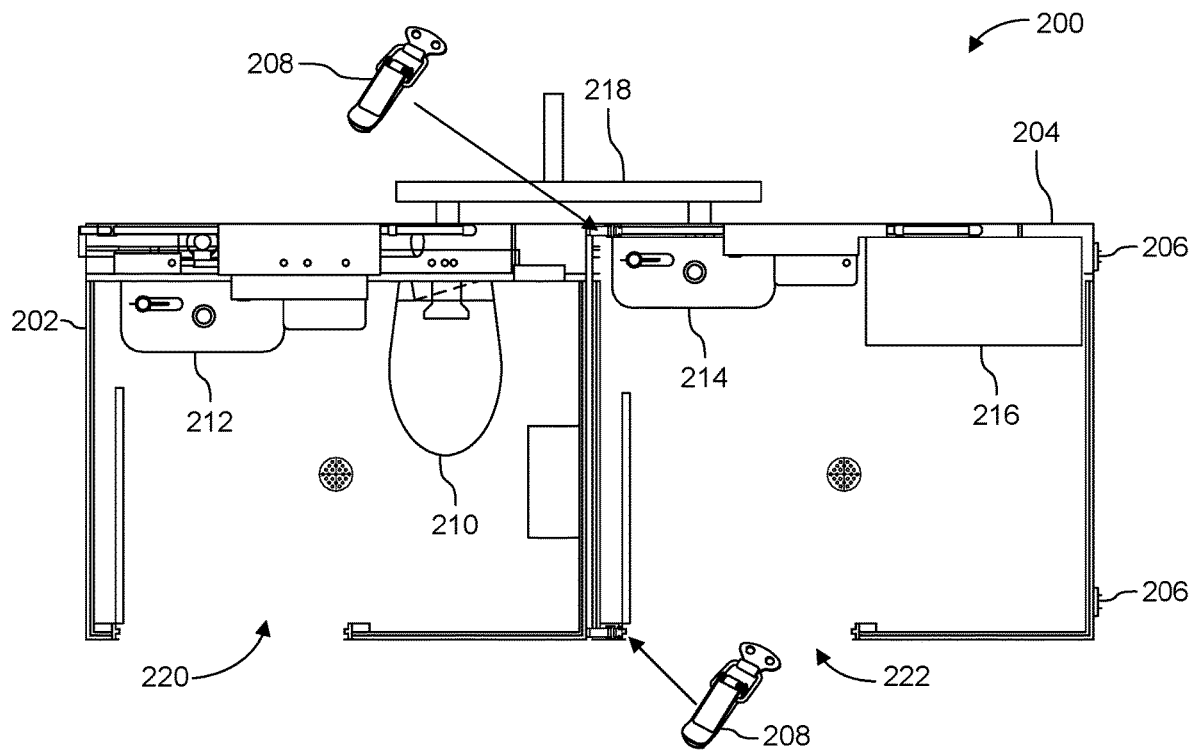
FIG. 13 is a top plan view of a temporary restroom and wellness pod system including one temporary restroom pod and one temporary break room pod, according to one embodiment.

Referring now to FIG. 13, one embodiment of a temporary restroom and wellness pod system 200 is illustrated in top view, with ceilings removed to show the floor plan. On some construction sites, a worker breakroom area (or "wellness center") is constructed on the ground floor of the site. This wellness center typically includes toilet rooms and a break room, which may include a sink and microwave, for example. On most construction sites, the wellness center is rudimentary and is not reusable—in other words, when construction is complete, the wellness center is torn down and thrown away with other construction refuse. The temporary restroom and wellness pod system 200 shown in FIG.

13 takes advantage of the modular nature of the temporary restrooms described above to combine a temporary restroom pod 202 with a break room pod 204, both of which are easily portable and can be moved to another site to be reused. In some embodiments, each "pod" 202, 204 of the system 200 includes multiple attachment features 206 (or "connectors") on one or both its outer sidewalls, to allow for easy connection with another pod 202, 204 in a side-by-side layout. The system 200 may also include multiple fasteners 208 (or "attachment members") to connect one pod 202 to another pod 204. The fasteners 208 may be any type of suitable fasteners, such as clasps, toggles, screws, bolts, hooks or the like.

In the pictured embodiment, the pod system 200 includes one temporary restroom pod 202 and one break room pod 204. The temporary restroom pod 202 may include any of the features described above, in any configuration and combination. This temporary restroom pod 202, for example, includes a toilet 210 and a sink 212, among other features. The break room pod 204 includes a sink 214 and a microwave 216 (or other kitchen appliance). The temporary restroom pod 202 includes a doorway 220, and the break room pod also includes its own doorway 222. These separate doorways 220, 222 help contribute to privacy and sanitary work conditions, since workers are not required, for example, to enter and exit a restroom through a break room. The pods 202, 204 are connected in back to common plumbing 218, thus facilitating water and waste management in the pods 202, 204. In various alternative embodiments, any number of temporary restroom pods 202 and break room pods 204 may be included in the system 200. Also, each temporary restroom pod 202 and each break room pod 204 may have any desired size and features, according to different embodiments. The various pods 202, 204 may be used, combined and even customized for different construction sites.

Figure 14:
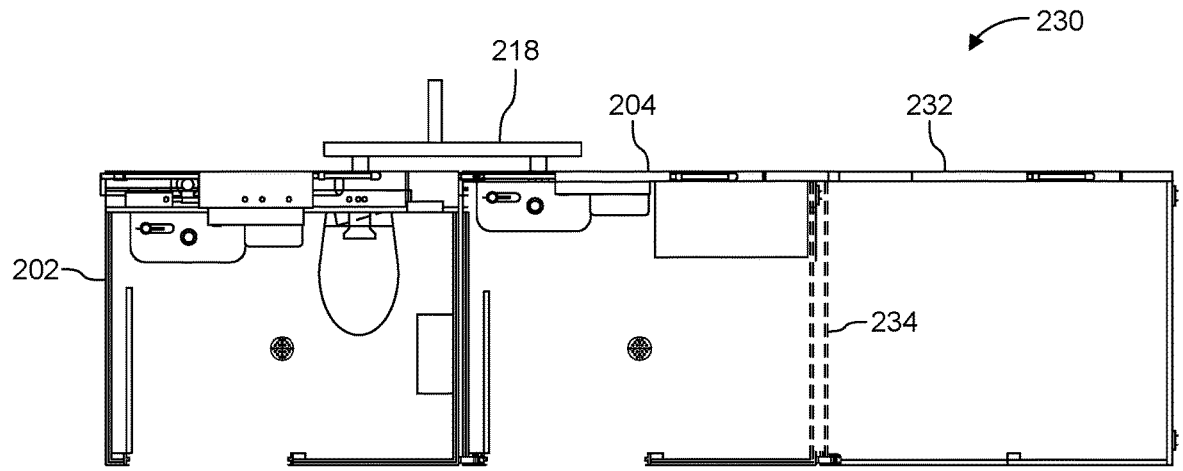
FIG. 14 is a top plan view of a temporary restroom and wellness pod system including one temporary restroom pod, one break room pod and an addition pod, according to an alternative embodiment.

Referring to FIG. 14, another temporary restroom and wellness pod system 230 is illustrated. This system 230 includes the same temporary restroom pod 202 and break room pod 204 as in FIG. 13, but it also includes an addition pod 232 attached to the break room pod 204 to increase the size of the break room 204. In some embodiments, one or more pods 202, 204, 232 may include a removable wall 234, which may be removed and stored in another location or may be retractable or partially retractable in various embodiments. The removable wall 234 between the break room pod 204 and the addition pod 232 allows for the expansion of the break room. Alternatively, there may be a door between the break room pod 204 and the addition pod 232 in other embodiments. In this embodiment, the addition pod 232 does not include any inside features but merely increases the inside space of the break room pod 204. Other embodiments may include any suitable features, as desired. As might be imagined, the temporary restroom and wellness pod system 230 may include any number, configuration and combination of temporary restroom pods 202, break room pods 204 and addition pods 232, in various embodiments.

Figure 15:
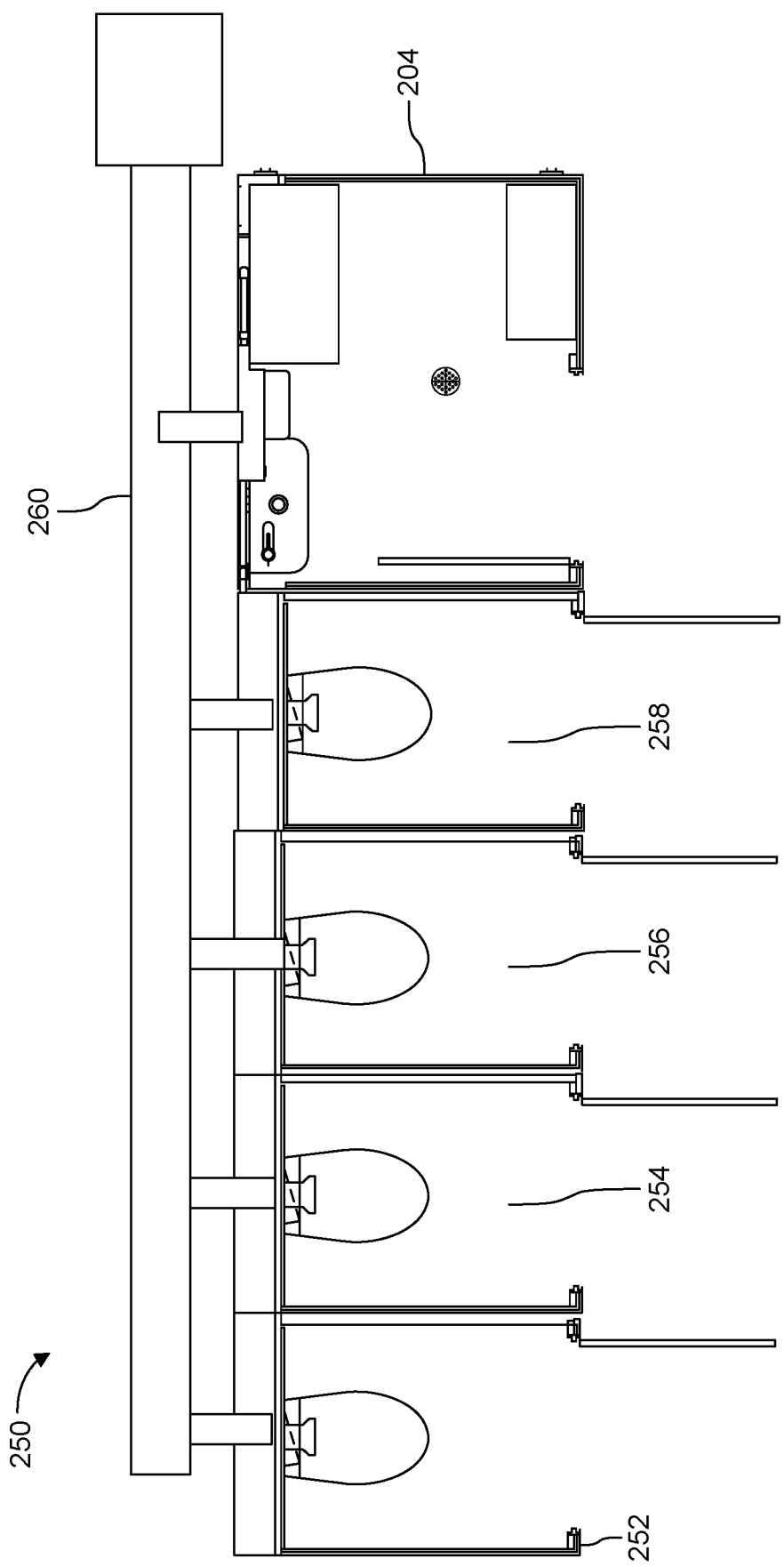
FIG. 15 is a top plan view of a temporary restroom and wellness pod system including four temporary restroom pods and one break room pod, according to another alternative embodiment.

FIG. 15 illustrates yet another embodiment of a multi-room temporary restroom and wellness pod system 250. In this embodiment, the break room pod 204 is attached at one end of a line of four temporary restroom pods 252, 254, 256, 258. The temporary restroom pods 252, 254, 256, 258 are simpler in this embodiment than in previously described embodiments. They are smaller and include primarily just a toilet. Although each temporary restroom pod 252, 254, 256, 258 would also at least include a toilet paper dispenser and a hand sanitizer dispenser, it may be that area constraints on some construction sites dictate smaller restrooms in greater quantity. The system 250 illustrated in FIG. 15 shows the modularity of the various temporary restroom and wellness pod embodiments and that different temporary restrooms, break rooms, and features of each can be interchanged to create different layouts. Again, a common plumbing system 260 may connect all the pods 204, 252, 254, 256, 258 of the system 250. As should already be apparent from FIGS. 13-15, any suitable configuration, combination and sizes of restroom pods, break room pods and/or addition pods may be used in any given embodiment.

The foregoing is believed to be a complete and accurate description of embodiments and aspects of the present invention. In various alternative embodiments, however, alterations may be made to any given embodiment, aspect or feature described above, without departing from the scope of the invention as it described in the following claims.

The invention claimed is:
1. A temporary restroom, comprising:
  an enclosure, comprising;
    a front wall;
    a back wall;
    two sidewalls;
    a floor;
    a ceiling; and
    a door on the front wall,
    wherein each of the front wall, the back wall, the two sidewalls, the floor and the ceiling comprises;
      multiple support members, wherein the multiple support members together form a frame configured so that the temporary restroom can be lifted off the ground; and
      at least one panel covering the multiple support members;
  a toilet in the enclosure, coupled with the back wall and a waste drainage pipe;
  a sink in the enclosure, coupled with the back wall, a water pipe and a waste water drainage pipe;
  a water heater coupled with the back wall and the water pipe;
  a heating, ventilation and air-conditioning (HVAC) unit in the enclosure, coupled with the back wall or one of the two sidewalls; and
  multiple wheels on a bottom of the temporary restroom.
2. The temporary restroom of claim 1, further comprising multiple additional features, wherein each of the multiple additional features is attached to the back wall or one of the two sidewalls, the multiple additional features comprising:
  a toilet paper dispenser;
  a sanitizer dispenser for dispensing at least one of soap or hand sanitizer;
  a hand drier; and
  a light.
3. The temporary restroom of claim 1, wherein the at least one panel covering the ceiling of the enclosure is at least partially translucent.
4. The temporary restroom of claim 1, further comprising:
  an ultraviolet light coupled with at least one of the ceiling, one of the two side walls or the back wall; and
  a motion sensor configured to detect motion of a user of the temporary restroom,
  wherein the ultraviolet light is configured to turn on automatically and remain illuminated for a preset amount of time when the motion sensor detects that no user is in the temporary restroom.

5. The temporary restroom of claim 1, wherein the at least one panel of the back wall comprises:
   at least one inner panel; and
   at least one outer panel, wherein the inner panel and the outer panel form a space therebetween.

6. The temporary restroom of claim 5, wherein the water heater is located inside the space between the inner panel and the outer panel, and wherein the space further contains:
   a common drainage pipe for receiving the waste drainage pipe and the waste water drainage pipe and connecting to a sewage pipe of a building under construction;
   an electrical panel; and
   a power connector for connecting the HVAC unit with an external source of electrical power.

7. The temporary restroom of claim 1, further comprising at least one handle on an outside surface for facilitating rolling the temporary restroom using the wheels.

8. The temporary restroom of claim 1, wherein no features inside the temporary restroom touch the floor, thus facilitating cleaning of the floor.

9. The temporary restroom of claim 1, wherein the temporary restroom is configured to be lifted off the ground using at least one of a lift or a crane.

10. A temporary restroom, comprising:
    an enclosure, comprising;
       a front wall;
       a back wall;
       two sidewalls;
       a floor;
       a ceiling; and
       a door,
       wherein each of the front wall, the back wall, the two sidewalls, the floor and the ceiling comprises multiple support members, which together form a frame;
    a toilet in the enclosure, coupled with a waste drainage pipe;
    a sink in the enclosure, coupled with a water pipe and a waste water drainage pipe; and
    multiple connections for connecting the waste drainage pipe and the waste drainage pipe to waste plumbing, connecting the water pipe to water plumbing, and connecting the temporary restroom to a source of electric power,
    wherein the temporary restroom does not include a waste storage tank or a built-in source of water;
    a water heater coupled with the water pipe;
    a heating, ventilation and air-conditioning (HVAC) unit; and
    multiple wheels on a bottom of the temporary restroom.

11. The temporary restroom of claim 10, further comprising:
    a toilet paper dispenser;
    a sanitizer dispenser for dispensing at least one of soap or hand sanitizer;
    a hand drier; and
    a light.

12. A temporary restroom, comprising:
    an enclosure, comprising;
       a front wall;
       a back wall;
       two sidewalls;
       a floor;
       a ceiling; and
       a door,
       wherein each of the front wall, the back wall, the two sidewalls, the floor and the ceiling comprises multiple support members, which together form a frame;
    a toilet in the enclosure, coupled with a waste drainage pipe;
    a sink in the enclosure, coupled with a water pipe and a waste water drainage pipe; and
    multiple connections for connecting the waste drainage pipe and the waste drainage pipe to waste plumbing, connecting the water pipe to water plumbing, and connecting the temporary restroom to a source of electric power,
    wherein the temporary restroom does not include a waste storage tank or a built-in source of water;
    wherein each of the front wall, the back wall, the two sidewalls, the floor and the ceiling comprises at least one panel attached to and covering the multiple support members, and wherein the at least one panel covering the ceiling of the enclosure is at least partially translucent.

13. A temporary restroom system, comprising:
    multiple restroom units, each of the multiple restroom units comprising;
       a toilet;
       a front wall;
       a back wall;
       two sidewalls;
       a floor;
       a ceiling;
       a door; and
       connection members on an outer surface of each of the two sidewalls, for connecting the multiple restroom units together; and
    multiple attachment members for attaching the connection members of one of the multiple restroom units with the connection members of another of the multiple restroom units,
    wherein none of the multiple restroom units includes a waste storage tank or a built-in source of water.

14. The temporary restroom system of claim 13, wherein each of the multiple restroom units further comprises at least one additional feature selected from the group consisting of a sink, a water heater, a heating, ventilation and air-conditioning (HVAC) unit, multiple wheels on a bottom of the restroom unit, a toilet paper dispenser, a sanitizer dispenser for dispensing at least one of soap or hand sanitizer, a hand drier, and a light.

15. The temporary restroom system of claim 13, wherein each of the front wall, the back wall, the two sidewalls, the floor and the ceiling comprises at least one panel attached to and covering multiple support members, and wherein the at least one panel covering the ceiling is at least partially translucent.

16. The temporary restroom system of claim 13, further comprising a break room unit that does not include a toilet, wherein the break room unit comprises compatible connection members to connect the break room unit with at least one of the multiple restroom units.

17. The temporary restroom system of claim 16, wherein the break room unit comprises a sink, the system further comprising a common waste pipe connection for connecting a waste pipe from at least one of the multiple restroom units and a waste water pipe from the sink with waste plumbing.

18. The temporary restroom system of claim 16, wherein the multiple restroom units, when attached to one another, are aligned side-by-side in a row, and wherein the break room unit is attached to a free side of one of the multiple restroom units at one end of the row.

19. The temporary restroom system of claim 13, wherein each of the multiple restroom units is sized and configured to be lifted to an above-ground-level floor of a construction site with at least one of a crane or a hoist.

\* \* \* \* \*